US012778494B2

(12) United States Patent
De Souza et al.

(10) Patent No.: US 12,778,494 B2
(45) Date of Patent: Nov. 3, 2026

(54) SYSTEMS AND METHODS FOR HOLISTIC HABITUAL IMPROVEMENT VIA DIGITAL SOLUTIONS

(71) Applicant: ResMed Digital Health Inc., San Diego, CA (US)

(72) Inventors: Sakeena De Souza, Sydney (AU); Michael James Dent, Bella Vista (AU); James Sung, Bella Vista (AU); Gregory Robert Peake, Sydney (AU); Andrew William Gillett, Bella Vista (AU)

(73) Assignee: ResMed Digital Health Inc., San Diego, CA (US)

( * ) Notice: Subject to any disclaimer, the term of this patent is extended or adjusted under 35 U.S.C. 154(b) by 304 days.

(21) Appl. No.: 18/219,085

(22) Filed: Jul. 6, 2023

(65) Prior Publication Data

US 2024/0008809 A1 Jan. 11, 2024

Related U.S. Application Data

(60) Provisional application No. 63/368,042, filed on Jul. 8, 2022.

(51) Int. Cl.
*A61B 5/00* (2006.01)

(52) U.S. Cl.
CPC .......... *A61B 5/4815* (2013.01); *A61B 5/4836* (2013.01); *A61B 5/742* (2013.01)

(58) Field of Classification Search
CPC ..... A61B 5/4815; A61B 5/4836; A61B 5/742; A61B 5/1118; A61B 5/4812
See application file for complete search history.

(56) References Cited

U.S. PATENT DOCUMENTS

| | | | | |
|---|---|---|---|---|
| 9,358,353 | B2 | 6/2016 | Armitstead et al. | |
| 2016/0051184 | A1* | 2/2016 | Wisbey | A61B 5/4815 600/595 |
| 2017/0189641 | A1* | 7/2017 | Moturu | G16H 20/70 |
| 2018/0042547 | A1* | 2/2018 | Raymann | A61B 5/4809 |
| 2018/0333558 | A1* | 11/2018 | Levendowski | A61B 5/4094 |
| 2020/0337470 | A1* | 10/2020 | Sayadi | A61B 5/4812 |

FOREIGN PATENT DOCUMENTS

WO 2008/138040 A1 11/2008

* cited by examiner

*Primary Examiner* — Joseph M Dietrich
(74) *Attorney, Agent, or Firm* — Nixon Peabody LLP

(57) ABSTRACT

A method includes receiving electronically data associated with physical or psychological factors of a user, the data being collected from (a) a plurality of smart home devices, (b) a plurality of mobile devices, or (c) both. The physical or psychological factors are based on at least one physical activity of the user. The method further includes identifying, based on the data, an effect on sleep quality of the user, based on which a remedial action is determined for improving sleep quality of the user. The method also includes causing the remedial action to be communicated in electronic form to the user in real-time during the physical activity, and automatically implementing, without input from the user, at least a part of the remedial action via one or more of the devices. The remedial action increases least one of a deep-sleep state and sleep duration of the user.

18 Claims, 7 Drawing Sheets

SYSTEMS AND METHODS FOR HOLISTIC HABITUAL IMPROVEMENT VIA DIGITAL SOLUTIONS

CROSS-REFERENCE TO RELATED APPLICATIONS

This application claims the benefit of, and priority to, U.S. Provisional Patent Application No. 63/368,042, filed Jul. 8, 2022, which is hereby incorporated by reference herein in its entirety.

TECHNICAL FIELD

The present disclosure relates generally to systems and methods for improving quality of sleep of a user, and more particularly, to systems and methods for suggesting a remedial health action based on a user activity.

BACKGROUND

Many individuals suffer from sleep-related and/or respiratory-related disorders such as, for example, Sleep Disordered Breathing (SDB), which can include Obstructive Sleep Apnea (OSA), Central Sleep Apnea (CSA), other types of apneas such as mixed apneas and hypopneas, Respiratory Effort Related Arousal (RERA), and snoring. In some cases, these disorders manifest, or manifest more pronouncedly, when the individual is in a particular lying/sleeping position. These individuals may also suffer from other health conditions (which may be referred to as comorbidities), such as insomnia (e.g., difficulty initiating sleep, frequent or prolonged awakenings after initially falling asleep, and/or an early awakening with an inability to return to sleep), Periodic Limb Movement Disorder (PLMD), Restless Leg Syndrome (RLS), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, and chest wall disorders.

These disorders are often adversely affected at least in part by bad habits or activities of a user. The present disclosure is directed to solving these and other problems.

SUMMARY

According to some implementations of the present disclosure, a method includes receiving electronically data associated with physical or psychological factors of the user, the data being collected from (a) a plurality of smart home devices, (b) a plurality of mobile devices, or (c) both. The physical or psychological factors are based on at least one physical activity of the user. The method further includes identifying, based on the data, an effect on sleep quality of the user, and determining, based on the effect, a remedial action for improving sleep quality of the user. The method also includes causing the remedial action to be communicated in electronic form to the user in real-time during the physical activity, and automatically implementing, without input from the user, at least a part of the remedial action via one or more of the plurality of smart home devices or the plurality of mobile devices. The method further includes increasing at least one of a deep-sleep state and sleep duration based on the remedial action.

According to some other implementations of the present disclosure, a method is directed to improving sleeping habits of a user. The method includes collecting activity data detected via (a) a plurality of smart home devices, (b) a plurality of mobile devices, or (c) both. The activity data is indicative of various physical activities of the user, at least some of the plurality of smart home devices and the plurality of mobile devices being communicatively coupled for sharing the activity data. The method further includes correlating the activity data to sleep quality that is specific to the user, the sleep quality including physical aches caused by sleeping posture. The method also includes determining, based on the correlating, a sleep effect on the sleep quality of the user, and generating, based on the sleep effect, a sleep-quality indicator. In response to changes in the activity data, the method further includes adjusting in real-time the sleep-quality indicator. The method further includes causing the sleep-quality indicator to be communicated to the user in real-time during the physical activity, and increasing at least one of a deep-sleep state and sleep duration based on the adjusting of the sleep-quality indicator.

According to some other further implementations of the present disclosure, a system includes an electronic interface configured to receive data associated with a physical activity of a user, and a memory storing machine-readable instructions. The system further includes a control system including one or more processors configured to execute machine-readable instructions. The machine-readable instructions include receiving electronically data associated with physical or psychological factors of the user. The data is collected from (a) a plurality of smart home devices, (b) a plurality of mobile devices, or (c) both. The physical or psychological factors are based on at least one physical activity of the user. The machine-readable instructions further include identifying, based on the data, an effect on sleep quality of the user, and determining, based on the effect, a remedial action for improving sleep quality of the user. The machine-readable instructions also include causing the remedial action to be communicated in electronic form to the user in real-time during the physical activity, and automatically implementing, without input from the user, at least a part of the remedial action via one or more of the plurality of smart home devices and the plurality of mobile devices. The machine-readable instructions further include increasing at least one of a deep-sleep state and sleep duration based on the remedial action.

The above summary is not intended to represent each implementation or every aspect of the present disclosure. Additional features and benefits of the present disclosure are apparent from the detailed description and figures set forth below.

Figure 1:
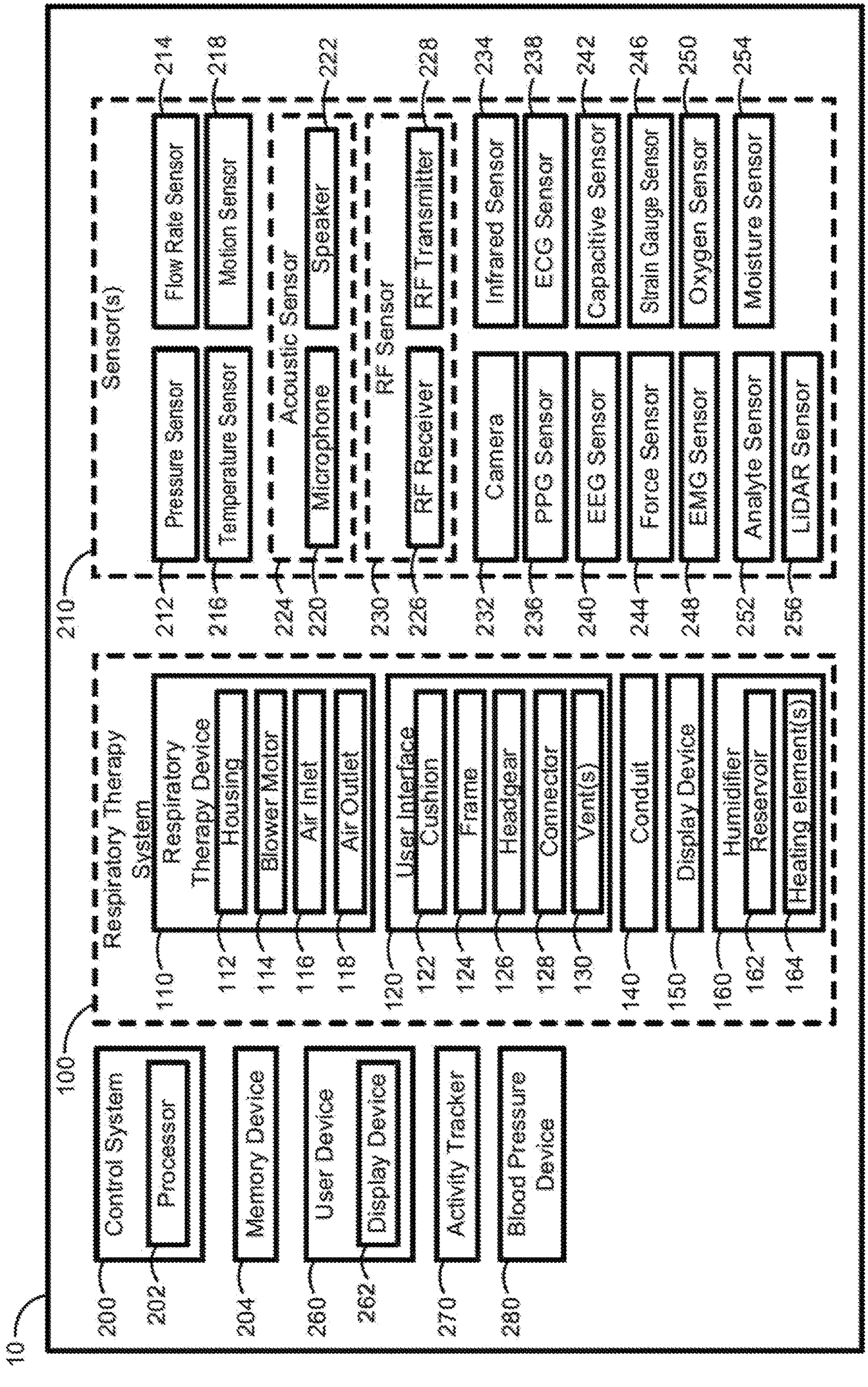
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from sleep-related and/or respiratory disorders, such as Sleep Disordered Breathing (SDB) such as Obstructive Sleep Apnea (OSA), Central Sleep Apnea (CSA) and other types of apneas, Respiratory Effort Related Arousal (RERA), snoring, Cheyne-Stokes Respiration (CSR), respiratory insufficiency, Obesity Hyperventilation Syndrome (OHS), Chronic Obstructive Pulmonary Disease (COPD), Periodic Limb Movement Disorder (PLMD), Restless Leg Syndrome (RLS), Neuromuscular Disease (NMD), and chest wall disorders.

Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). CSA results when the brain temporarily stops sending signals to the muscles that control breathing. Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events fulfil the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., the disclosure of each of which is hereby incorporated by reference herein in their entireties.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. COPD encompasses a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 10, according to some implementations of the present disclosure, is illustrated. The system 10 includes a respiratory therapy system 100, a control system 200, one or more sensors 210, a user device 240, and an activity tracker 250.

The respiratory therapy system 100 includes a respiratory pressure therapy (RPT) device 110 (referred to herein as respiratory therapy device 110), a user interface 120 (also referred to as a mask or a patient interface), a conduit 140 (also referred to as a tube or an air circuit), a display device 150, and a humidifier 160. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 100 is generally used to treat individuals suffering from one or more sleep-related respiratory disorders (e.g., obstructive sleep apnea, central sleep apnea, or mixed sleep apnea).

The respiratory therapy system 100 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

The respiratory therapy device 110 is generally used to generate pressurized air that is delivered to a user (e.g., using one or more motors that drive one or more compressors). In some implementations, the respiratory therapy device 110 generates continuous constant air pressure that is delivered to the user. In other implementations, the respiratory therapy device 110 generates two or more predetermined pressures (e.g., a first predetermined air pressure and a second predetermined air pressure). In still other implementations, the respiratory therapy device 110 generates a variety of different air pressures within a predetermined range. For example, the respiratory therapy device 110 can deliver at least about 6 $cmH_2O$, at least about 10 $cmH_2O$, at least about 20 $cmH_2O$, between about 6 $cmH_2O$ and about 10 $cmH_2O$, between about 7 $cmH_2O$ and about 12 $cmH_2O$, etc. The respiratory therapy device 110 can also deliver pressurized air at a predetermined flow rate between, for example, about −20 L/min and about 150 L/min, while maintaining a positive pressure (relative to the ambient pressure).

The respiratory therapy device 110 includes a housing 112, a blower motor 114, an air inlet 116, and an air outlet 118. The user interface 120 engages a portion of the user's face and delivers pressurized air from the respiratory therapy device 110 to the user's airway to aid in preventing the airway from narrowing and/or collapsing during sleep. This may also increase the user's oxygen intake during sleep. Generally, the user interface 120 engages the user's face such that the pressurized air is delivered to the user's airway via the user's mouth, the user's nose, or both the user's mouth and nose. Together, the respiratory therapy device 110, the user interface 120, and the conduit 140 form an air pathway fluidly coupled with an airway of the user. The pressurized air also increases the user's oxygen intake during sleep. Depending upon the therapy to be applied, the user interface 120 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 $cmH_2O$.

The user interface 120 can include, for example, a cushion 122, a frame 124, a head gear 126, connector 128, and one or more vents 130. The cushion 122 and the frame 124 define a volume of space around the mouth and/or nose of the user. When the respiratory therapy system 100 is in use, this volume space receives pressurized air (e.g., from the respiratory therapy device 110 via the conduit 140) for passage into the airway(s) of the user. The headgear 126 is generally used to aid in positioning and/or stabilizing the user interface 120 on a portion of the user (e.g., the face), and along with the cushion 122 (which, for example, can comprise silicone, plastic, foam, etc.) aids in providing a substantially air-tight seal between the user interface 120 and the user 20. In some implementations the headgear 126 includes one or more straps (e.g., including hook and loop fasteners). The connector 128 is generally used to couple (e.g., connect and fluidly couple) the conduit 140 to the cushion 122 and/or frame 124. Alternatively, the conduit 140 can be directly coupled to the cushion 122 and/or frame 124 without the connector 128. The vent 130 can be used for permitting the escape of carbon dioxide and other gases exhaled by the user 20. The user interface 120 generally can include any suitable number of vents (e.g., one, two, five, ten, etc.).

Figure 2:
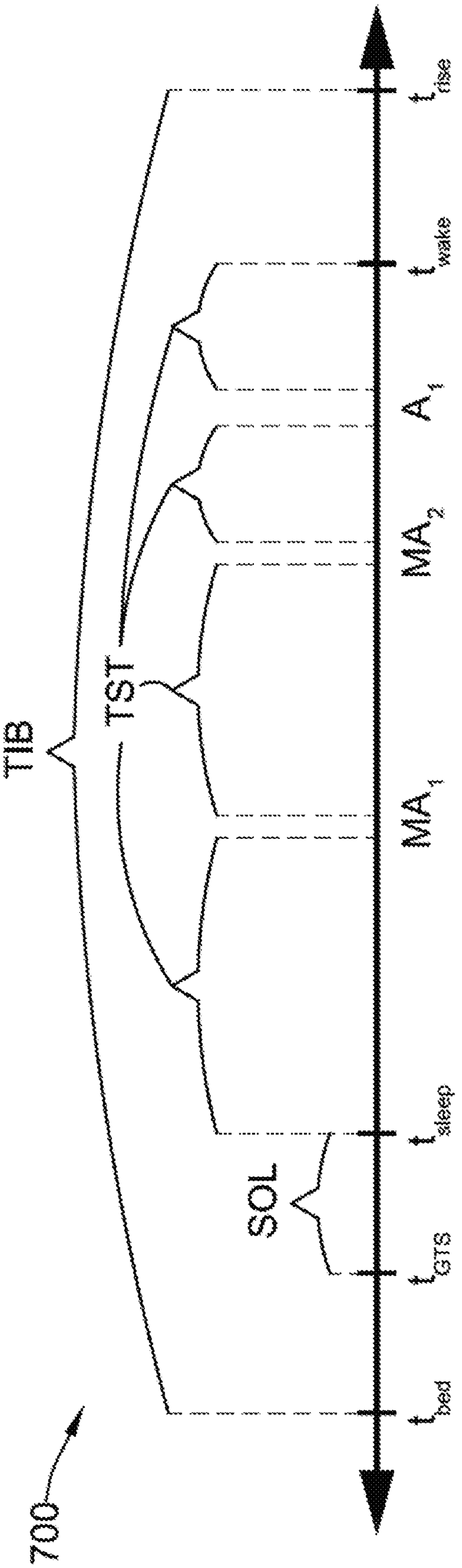
FIG. 2 illustrates an exemplary timeline for a sleep session, according to some implementations of the present disclosure.

Referring to the timeline 700 in FIG. 2 the enter bed time $t_{bed}$ is associated with the time that the user initially enters the bed prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed (bed). For example, after entering the bed, the user may engage in one or more activities to wind down prior to trying to sleep (e.g., reading, watching TV, listening to music, using the user device 260, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 700 of FIG. 2, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time (teed) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time (teed) and ending at the wake-up time ($t_{wake}$). In some implementations, a sleep session is defined as starting at the initial sleep time ($t_{sleep}$) and ending at the rising time ($t_{rise}$).

Figure 3:
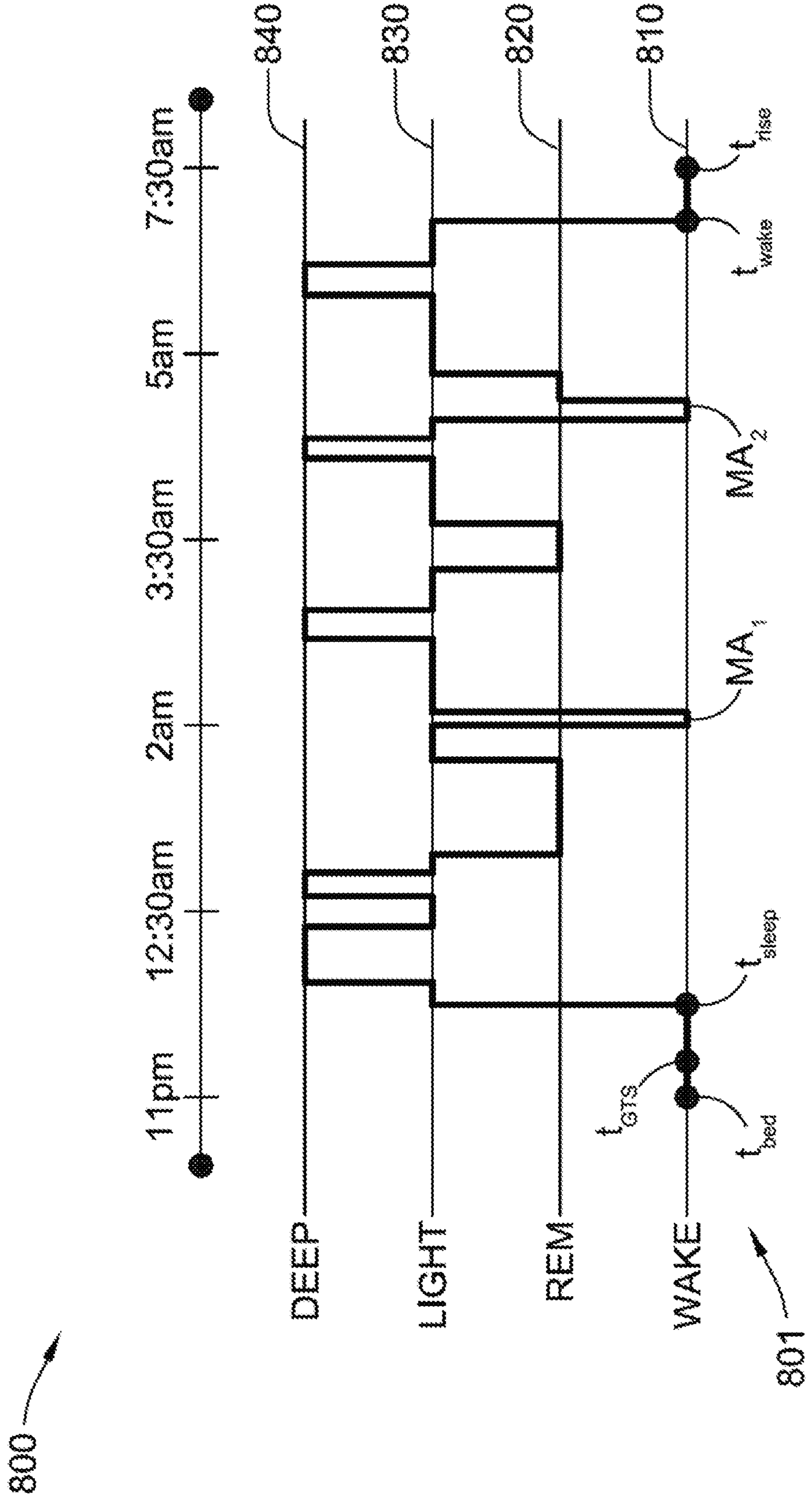
FIG. 3 illustrates an exemplary hypnogram associated with the sleep session of FIG. 2, according to some implementations of the present disclosure.

Referring to FIG. 3, an exemplary hypnogram 800 corresponding to the timeline 700 (FIG. 2), according to some implementations, is illustrated. As shown, the hypnogram 800 includes a sleep-wake signal 801, a wakefulness stage axis 810, a REM stage axis 820, a light sleep stage axis 830, and a deep sleep stage axis 840. The intersection between the sleep-wake signal 801 and one of the axes 810-840 is indicative of the sleep stage at any given time during the sleep session.

The sleep-wake signal 801 can be generated based on physiological data associated with the user (e.g., generated by one or more of the sensors 210 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 800 is shown in FIG. 3 as including the light sleep stage axis 830 and the deep sleep stage axis 840, in some implementations, the hypnogram 800 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 204.

The hypnogram 800 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 2), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 2), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time (teed), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 210 can be used to determine or identify the enter bed time (bed), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time teed can be determined based on, for example, data generated by the motion sensor 218, the microphone 220, the camera 232, or any combination thereof. The go-to-sleep time can be determined based on, for example, data from the motion sensor 218 (e.g., data indicative of no movement by the user), data from the camera 232 (e.g., data indicative of no movement by the user and/or that the user has turned off the lights) data from the microphone 220 (e.g., data indicative of the using turning off a TV), data from the user device 260 (e.g., data indicative of the user no longer using the user device 260), data from the pressure sensor 212 and/or the flow rate sensor 214 (e.g., data indicative of the user turning on the respiratory therapy device 110, data indicative of the user donning the user interface 120, etc.), or any combination thereof.

Referring generally to FIGS. 4-7, a method and system is described for improving sleeping habits of a user in combination with or separately from any of the features described above in FIGS. 1-3. According to one example the method is provided in which data is passively collected from daily routines of the user, and remedial action is suggested to the user in real-time to increase better sleep habits. By way of a specific example, the method provides a live prescription for better sleep in response to daily activities of the user. The method is not limited to insomnia or sleep disorders, but includes any state that negatively impacts the sleep quality of the user. Furthermore, the method is performed in real-time to provide the user with the enhanced benefit of knowing exactly when something occurs or when an action should be taken.

The data includes (but is not limited to) one or more of the following health elements:

- sleep routine, which generally refers to the user going to be at a decent hour and/or getting sufficient hours of sleep;
- screen time (e.g., blue light);
- ambient temperature;
- ambient light;
- user temperature;
- user position (e.g., in a chair, in bed, on a couch)
- ambient humidity;
- use of devices;
- sleep duration;
- duration of body movements;
- detected snoring
- blood pressure;
- heartbeat or heart rate;
- eye shape;
- sluggishness of user, especially during morning hours (e.g., compare user physical characteristics between morning and evening hours)
- exercise during the day;
- diet;
- wellness (e.g., anxiety, depression);
- outdoor time; and/or
- stress.

The data is received from respective sensors and is optionally controlled through a user device, such as an iPhone. For example, a light sensor measures intensity and/or duration of light, and then compares artificial vs. natural light. Based on the measurement and comparison, a remedial action is suggested to the user for improving sleep quality.

According to one optional feature of the present disclosure, devices with which the user interacts during the day or evening are monitored. For example, usage of a television set, a computer display, and/or a sound system is monitored to determine sleep-quality effects on the user. In another example, a refrigerator is monitored to determine input and/or output of food as it relates to the sleep-quality of the user. By way of a specific example, if (high sugar content) soda cans are constantly stored and removed from the refrigerator in the early evening, a remedial action is suggested to the user to "STOP consuming high sugar content items, so close to sleep, because there is a high likelihood that sleep will be affected," or reduce intake of soda, and, instead, drink more water.

According to another optional feature of the present disclosure, a fitness tracking device and/or a video camera is communicatively coupled to the disclosed system for providing movement of the user. Based on the movement, remedial actions are provided to the user. For example, if the user has been sitting in a chair for several hours, a notification reminds the user to stand up and get some exercise. Additionally or alternatively, the disclosed system automatically takes a remedial action, such as automatically lifting the user's chair, turning off a computer display, or otherwise physically directing the user to implement the suggested remedial action, to achieve better sleep.

According to one example, a health meter pops up automatically on the user's device, such as an iPhone of the user, showing the user where each one of the above health elements is in reference to an ideal condition. For example, if the user has not been outdoors yet, and it's the middle of the afternoon, an "Outdoor Time" indicator shows a blinking red light to stop indoor activities and go outdoors for some sun exposure. In another example, a meter fills-up as activities improve and depletes as activities are reduced.

The disclosed method or system is configured to tell a user, such as a patient, how personal choices during the day affect sleep at night. Data from the daily activities are passively collected and used to provide the prescription to the user for improved sleep. A health meter automatically adjusts in real-time to show which choices require a change in action. As such, the user is prompted during the day with live updates to make required changes for improved sleep.

Optionally, the system is synchronized with a calendar that provides automatic reminders. For example, the calendar prompts the user to eat lunch at a specific place with a specific food.

According to one beneficial aspect, the disclosed method or system provides personalized feedback and/or gamification aspects. For example, a notification is sent to the user towards the end of the day encouraging the user with "Great Work! You're going to have the best sleep tonight!" As a further example, the notification is followed-up the next morning requesting feedback from the user (e.g. "How did you sleep?") with suggested improvements, a summary of the previous day's lifestyle, and/or a modification of daily suggestions based on user feedback.

The disclosed method or system is optionally configured to receive electronic data from one or more devices, such as smart home devices, mobile devices, or both. For example, the devices include connected devices via smart home solutions (e.g., lights, music), app integration (e.g., push notifications, customized recommendations), and/or wearables (e.g., smartwatch).

The disclosed method or system is optionally integrated with smart home solutions. For example, the smart home solutions send a message to the user when it is time to prepare for bed, when to dim the lights, when to play relaxing music, and so on. Optionally, the smart home solutions automatically take a required action without user input (e.g., the smart home solutions automatically dim the lights and/or play the relaxing music).

According to some aspects of the present disclosure, useful insights are provided for a user health profile based on day and/or night activities of the user. For example, the insights include an impact on user sleep quality based on how much screen time the user has spent on a phone or TV, measurement of user movements, and/or number of user conferences or meetings. As such, the data is used to encourage the user take control of the user sleep quality, including data related to user diet, including food intake (such as intake of calories).

An exemplary benefit of the disclosed system and method is that the user is provided with feedback that is tailored for and specific to the individual user. Some examples of individually-tailored actions include measuring exertion levels of the user; providing sleeping input to the user based on those exertion levels; detecting user sleep patterns and personalizing feedback based on those sleep patterns; and detecting app usage or screen time before user bedtime.

Other exemplary benefits of the disclosed system and method include tapping into a vast, different eco-system that is more than just individual elements. For example the vast eco-system includes more than just screen time or physical data by itself. The personalization aspect resulting from the disclosed system and method overcomes prior problems in which generalization of certain data fails to adequately improve a user sleep quality or sleep health.

According to one optional feature of the present disclosure, data privacy is provided via on-device data collection and/or processing, or via a data anonymizer. The data privacy is optionally achieved via a standalone device that pairs with other devices.

According to another optional feature of the present disclosure, a user screen time is combined with one or more of a facial scan, actigraphy, and acoustic sleep detection to indicate improvements or to suggest other changes for improving sleep. For example, to optimize sleep, a remedial action includes exercising on particular times and using a mobile phone only at certain times.

According to another optional feature of the present disclosure, psychological data is collected using a daily survey to track the mood of the user. Optionally, a questionnaire determines a mental health of the user, based on which a sleep health solution is catered.

According to another optional feature of the present disclosure, the disclosed system and method monitor data collected via as many sensors worn by the user as possible. The data is aggregated and analyzed on-device to maximize or completely protect the privacy of the user.

According to another optional feature of the present disclosure, the disclosed system and method include supplemental consumer features that provide direct or indirect benefits for user sleep health. For example, a free alarm clock is included as a bonus feature for the user.

Yet another beneficial feature of the present disclosure is that the user is provided with improved sleep quality. Generally, good sleep is based on a mixture of adequate sleep stage and sleep duration. The remedial actions of the disclosed system and method improve the user time in one or more of the deep sleep state and the duration of the sleep.

Good sleep is also represented in part by duration, and number of sleep cycles achieved. For example, seven sleep cycles is a good indicator that the user has had a goodnight sleep.

Figure 4:
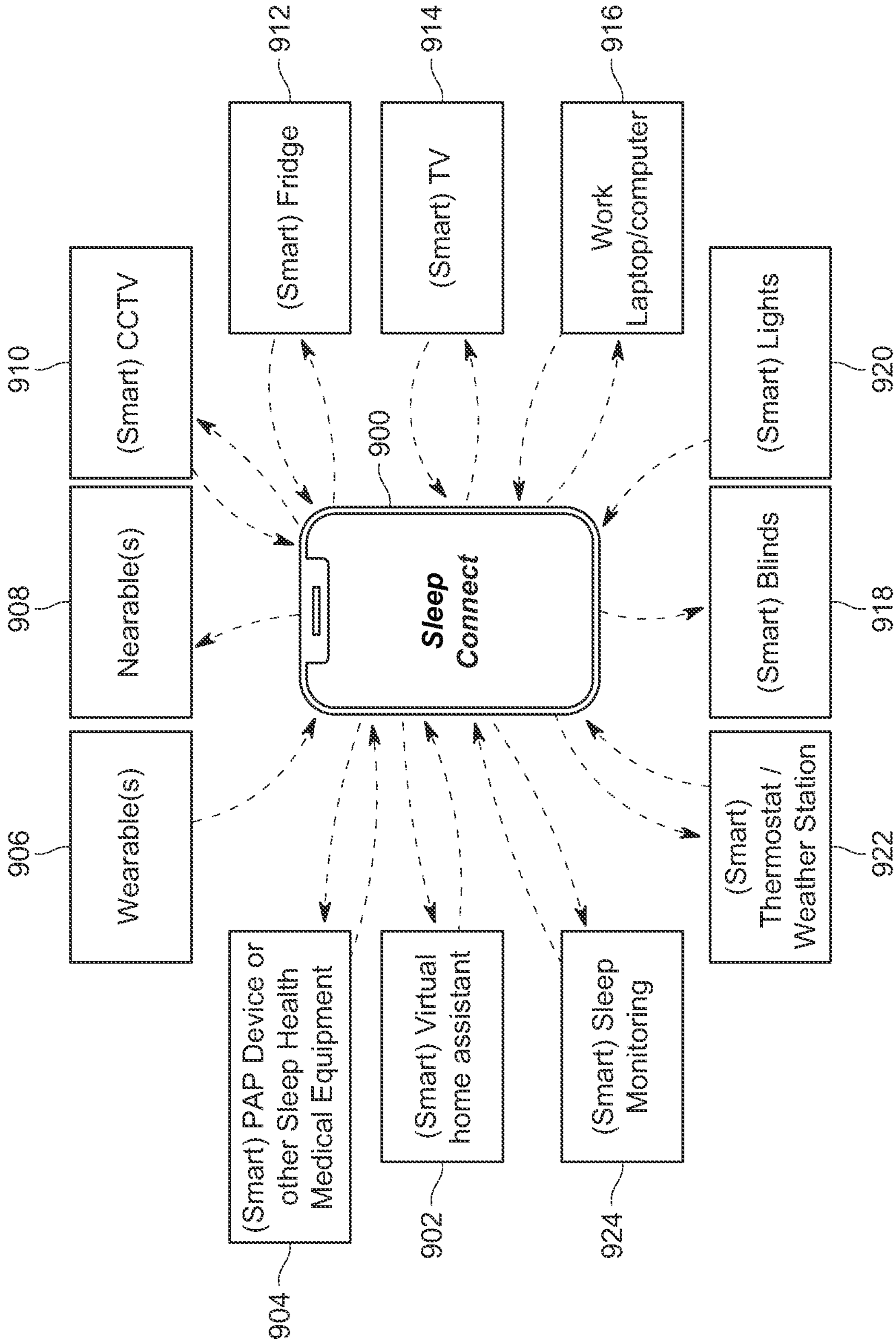
FIG. 4 is a diagrammatic illustration of a system for improving sleeping habits of a user, according to some implementations of the present disclosure.

Referring now specifically to FIG. 4, a Sleep Connect user device 900 is communicatively coupled to a plurality of smart home devices and/or a plurality of mobile devices. The Sleep Connect user device 900 collects activity data from one or more of the smart home devices and mobile devices, as indicated by the arrow direction from the respective smart home devices and mobile devices to the Sleep Connect user device. The Sleep Connect user device further outputs an adjustment to one or more of the smart home devices and mobile devices, as indicated by the arrow direction from the Sleep Connect user device to the respective smart home devices and mobile devices. Each of the illustrated exemplary smart home devices and mobile devices is described below with exemplary input or output features.

A (Smart) Virtual home assistant 902 provides input to the Sleep Connect user device 900 in the form of noise levels. The Sleep Connect user device 900 provides output in the form of environmental/noise level recommendations.

A (Smart) PAP Device 904, or other Sleep Health Medical Equipment, provides input to the Sleep Connect user device 900 in the form of a breathing rate (e.g., which may be indicative of anxiety or stress) or apnea-hypopnea index (AHI). The Sleep Connect user device 900 provides output in the form of sleep quality metrics and/or personalization of the (Smart) PAP Device 904, or other Sleep Health Medical Equipment.

Wearable(s) 906, Nearable(s) 908, and/or Earable(s) provide input to the Sleep Connect user device 900 in the form of:

- global positioning system (GPS) data;
- steps (indicative of movement);
- health kit, such as
  - blood pressure,
  - electrocardiogram (ECG),
  - heart rate,
  - pulse oximeter (SPO2),
  - atrial fibrillation (AFib); and/or
- galvanic skin response (GSR) as a predictor for anxiety, stress, and/or depression.

The Sleep Connect user device 900 provides output in the form of activity tracking, wellbeing tracking, environment tracking, etc. Key metrics determine sleep quality based on one or more of the above sleep health elements.

A (Smart) closed-circuit television (CCTV) 910 provides input to the Sleep Connect user device 900 in the form of outdoor activity data, such as yard and exercise time of the user. The Sleep Connect user device 900 provides output in the form of outdoor recommendations for the user.

A (Smart) fridge 912 provides input to the Sleep Connect user device 900 in the form of diet data, such as what food or drink products go in and out. The fridge 912 may also provide information corresponding to the person (e.g., user, assistant, relative) that stocks the fridge 912 or removes products from the fridge 912. Based on fridge contents or other fridge information, the Sleep Connect user device 900 provides output in the form personalized dietary recommendations, automated online shopping recommendations, and/or healthy recipes for better sleep.

A (Smart) television set (TV) 914 provides input to the Sleep Connect user device 900 in the form of a nightly routine of the user, and/or a blood pressure rising based on TV watching habits of the user. For example, the blood pressure changes between watching a sports show or a horror movie. The Sleep Connect user device 900 provides output in the form of a viewing recommendation and/or a screen time recommendation for the user. Optionally, the recommendations are automatically implemented in whole or in part. For example, a notification on the TV 914 indicates to the user that the channel will be changed because user's blood pressure historically and/or presently is outside a desired range.

A work laptop or computer 916 provides input to the Sleep Connect user device 900 in the form of one or more of a user routine, diary synchronization, calendar synchronization, video call tiredness indicator, stress indication data point. The Sleep Connect user device 900 provides output in the form of one or more of a screen time recommendation, a routine and activity recommendation, and a scheduling recommendation.

One or more (Smart) blinds 918 and/or (Smart) lights 920 provide input to the Sleep Connect user device 900 in the form house lighting levels (e.g., lumens). The Sleep Connect user device 900 provides output in the form of one or more of environment setup, lighting recommendation, ambiance recommendation, lighting control, and ambiance control.

A (Smart) thermostat and/or weather station 922 provide input to the Sleep Connect user device 900 in the form of a house climate and/or weather. The Sleep Connect user device 900 provides output in the form of environmental setup, temperature recommendation, temperature control, humidity recommendation, and/or humidity control.

A (Smart) sleep monitoring device 924 provides input to the Sleep Connect user device 900 in the form of sleep quality metrics, which include, by way of example, metrics for sleep stages, stillness, sleep time, awake hours, and/or asleep hours. The Sleep Connect user device 900 provides output in the form of a routine recommendation and/or adjustment of sleep quality levels to allow for personalized sleep formula.

Figure 5:
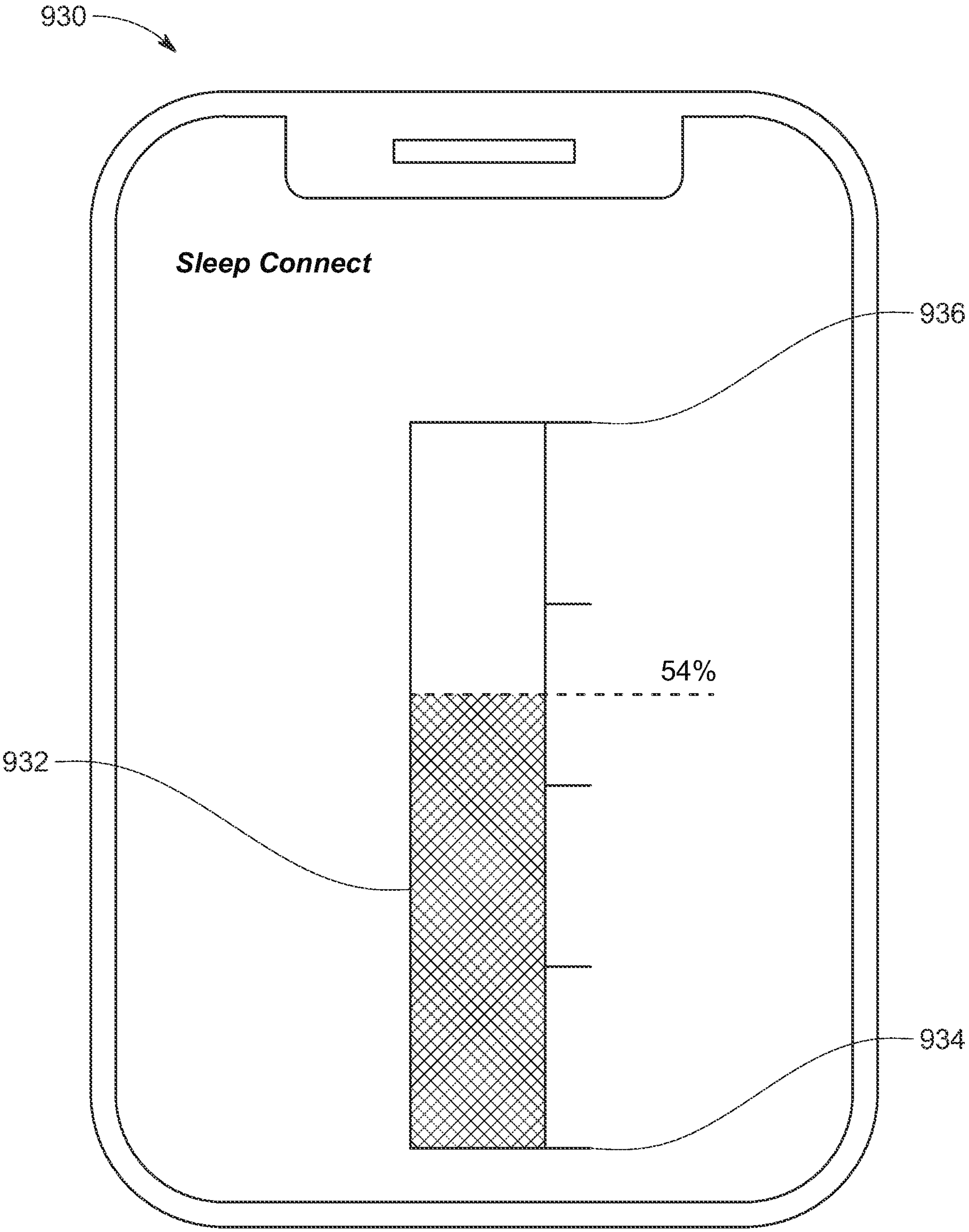
FIG. 5 is a representative illustration of an electronic device display showing a representative sleep quality indicator, according to some implementations of the present disclosure.

Referring to FIG. 5, an exemplary embodiment shows a display of a Sleep Connect user device 930 illustrating a sleep health-meter 932 representative of user sleep health. According to the illustrated example, the sleep-health meter 932 ranges from a minimum sleep-health 934 to a maximum sleep-health 936. The minimum sleep-health 934 is represented, by way of example, of the user being awake (or up) all night. The maximum sleep-health 936 is represented, by way of example, of the user having the highest chance of a best sleep. As currently represented, the sleep health-meter 932 shows a 54% chance of achieving a good sleep. The sleep health-meter 932 fills up or depletes based on the data collected for improving the sleep quality of the user.

Figure 6:
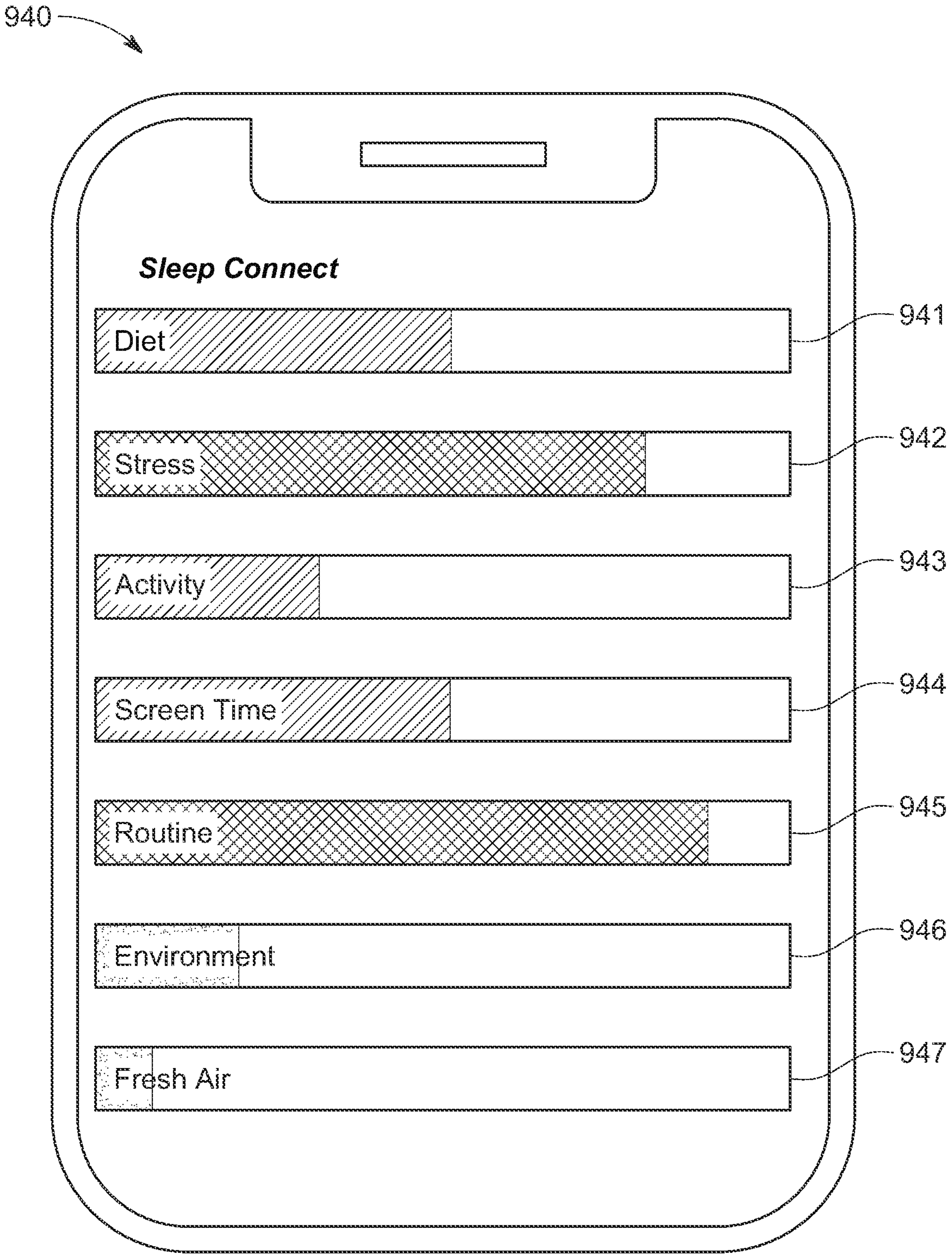
FIG. 6 is a representative illustration of an electronic device display showing physical and psychological data of a user for sleep improvement of a user, according to some implementations of the present disclosure.

Referring to FIG. 6, another exemplary embodiment shows a display of a Sleep Connect user device 940 illustrating a plurality of data health-meters 941-947, which are indicative of respective health contributors that affect the sleep quality of the user. For example, the data health-meters include (but are not limited to) the following:

- a diet health-meter 941 that shows a generally average user diet;
- a stress health-meter 942 that shows a better than average user stress level;
- an activity health-meter 943 that shows a less than average user physical activity;

a screen time health-meter 944 that shows close to average user usage of a screen, display, or monitor;

a routine health-meter 945 that shows very good user sleep routine implementation;

an environment health-meter 946 that shows poor environmental aspects for the user; and a fresh air health-meter 947 that shows a very poor fresh air environment for the user.

As shown in FIG. 6, the data health-meters 941-947 are presented as horizontal bars. The data health-meters 941-947 may be presented in other suitable forms, including presenting the data on a scale of 0-100, with 100 being the best score. The data health-meters 941-947 help focus the user on which changes are required to improve the sleep quality. Optionally, each of the data health-meters 941-947 contribute to adjusting the overall sleep health-meter 932 illustrated in FIG. 5.

Figure 7:
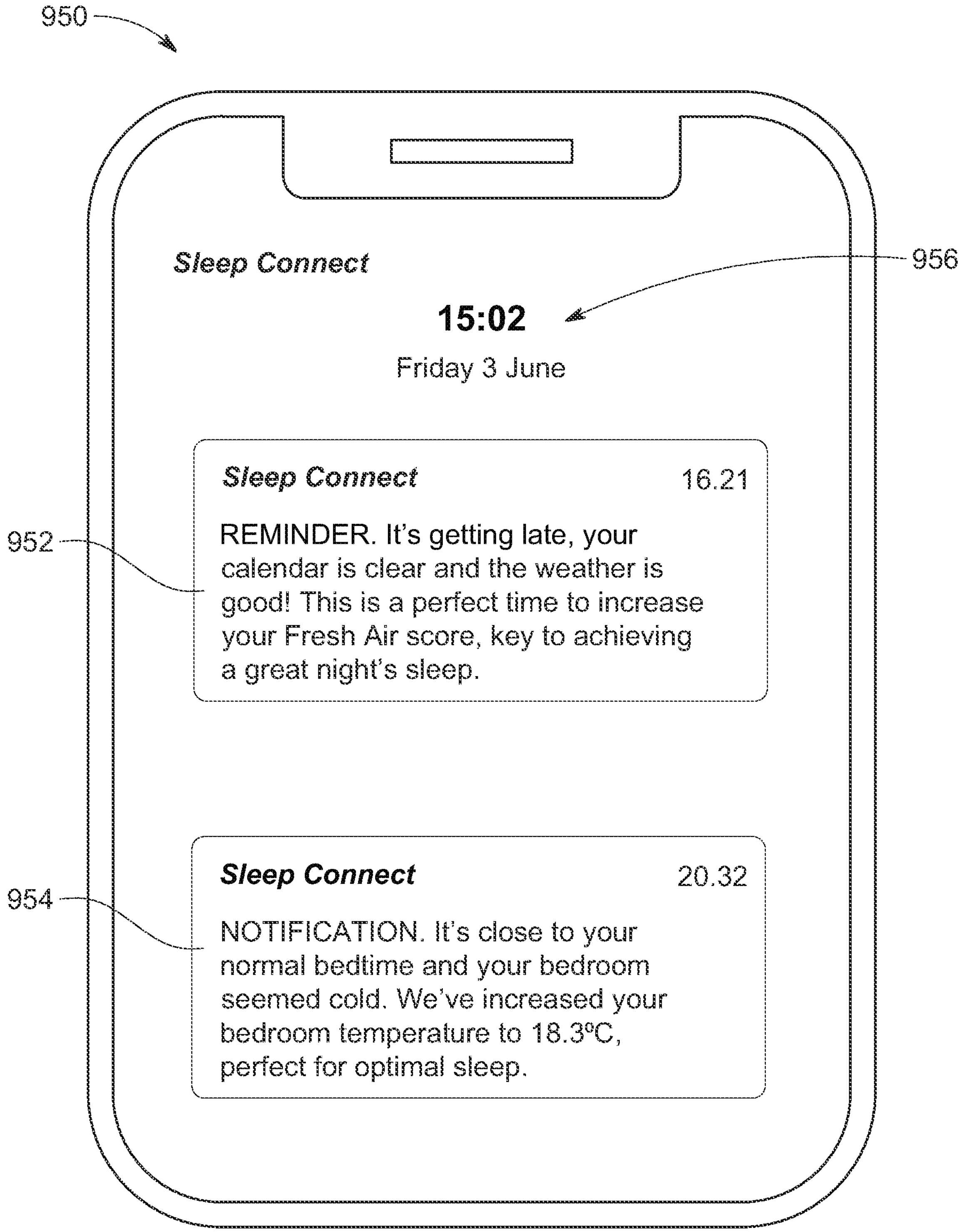
FIG. 7 is a representative illustration of an electronic device display showing a notification and a reminder for sleep improvement of a user, according to some implementations of the present disclosure.

Referring to FIG. 7, another example embodiment shows a display of a Sleep Connect user device 950 illustrating reminders and/or notifications related to the sleep quality of the user. For example, the fresh air health-meter 947 in FIG. 6 shows a very poor fresh air environment for the user, and, thus, a reminder 952 prompts the user to take the action of getting fresh air. The reminder optionally includes additional information reminding the user that the time is late (e.g., time shown as 16.21 or 4.21 pm), there are no further events scheduled, and the weather is good for walking or otherwise spending time outdoors. Spending time outdoors will, consequently, increase the fresh air score, which, in turn, will help improve the sleep quality of the user.

In another example, the notification 954 also shows an automated action performed for the user, without requiring any intervention or other action by the user. For example, the notification 954 shows that a bedroom temperature has been increased to an optimal sleeping temperature of "18.3° C.," from a previous colder temperature. Optionally, the Sleep Connect user device 950 shows the day and current time 956, functioning also as a clock and calendar.

According to a specific illustrative embodiment, a method includes receiving electronically data associated with physical or psychological factors of the user, the data being collected from (a) a plurality of smart home devices, (b) a plurality of mobile devices, or (c) both. The data is selected from any of the inputted information received from the smart devices or mobile devices described above in reference to FIG. 4. The physical or psychological factors are based on at least one physical activity of the user, including any physical activity described above in reference to FIG. 4, such as steps indicative of movement, activity tracking, etc.

The method further includes identifying, based on the data, an effect on sleep quality of the user, and determining, based on the effect, a remedial action for improving sleep quality of the user. For example, the effect on the sleep quality is determined via an algorithm of a control system, such as control system 200 illustrated in FIG. 1, based on the aggregated factors and a performed comparison. The comparison is optionally performed relative to previous data of the user, data of other users, and other information.

The method also includes causing the remedial action to be communicated in electronic form to the user in real-time during the physical activity, and automatically implementing, without input from the user, at least a part of the remedial action via one or more of the plurality of smart home devices or the plurality of mobile devices. The remedial action is optionally any of the outputted information received from the Sleep Connect user device described above in reference to FIG. 4.

The method further includes increasing at least one of; quantity of deep-sleep state occurrences, time spent within a deep-sleep state and sleep duration based on the remedial action. This is one of the end-goals for the user, in which the sleep quality is increased (or enhanced) by increasing components of the sleep quality, e.g., deep-sleep state or sleep duration.

One or more elements or aspects or steps, or any portion (s) thereof, from one or more of any of claims 1 to 15 below can be combined with one or more elements or aspects or steps, or any portion(s) thereof, from one or more of any of the other claims 1 to 15 or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:

receiving electronically data associated with physical or psychological factors of the user, the data being collected from (a) a plurality of smart home devices, (b) a plurality of mobile devices, or (c) both, the physical or psychological factors being based on at least one physical activity of the user;

identifying, based on the data, an effect on sleep quality of the user;

determining, based on the effect, a remedial action for improving sleep quality of the user;

causing the remedial action to be communicated in electronic form to the user in real-time during the physical activity, wherein the remedial action is communicated to the user at least in part in the form of a visual remedial indicator generated in the form of a meter image that is displayed on a screen of a mobile device of the user, the meter image being automatically adjusted in real-time to provide a live prescription for better sleep in response to changes in the data associated with the physical or psychological factors of the user;

automatically implementing, without input from the user, at least a part of the remedial action via one or more of the plurality of smart home devices or the plurality of mobile devices;

after the user has slept, receiving sleep-quality data for at least one sleep session of the user, the sleep-quality data including at least one of sleep stages, sleep duration, awake hours, and asleep hours;

correlating the sleep-quality data with the data associated with the physical or psychological factors of the user to determine a sleep effect on the sleep quality of the user attributable to one or more of the remedial actions;

adjusting, based on the sleep effect, at least one subsequent remedial action and subsequent automatic implementation so that later-computed remedial actions and meter images are personalized to the user's sleep patterns and lifestyle; and increasing at least one of a deep-sleep state and sleep duration based on the remedial action.

2. The method of claim 1, further comprising receiving the data wirelessly, the plurality of smart home devices and the plurality of mobile devices being communicatively coupled to an electronic device of the user.

3. The method of claim 2, wherein the plurality of smart home devices include at least one of a smart thermostat, a smart outlet, and a smart TV.

4. The method of claim 2, wherein the electronic device of the user includes at least one of a mobile phone and a smart watch wearable.

5. The method of claim 1, wherein the data includes at least one of sleep routine data, screen time data, physical exercise data, diet data, wellness data, outdoor time data, and stress data.

6. The method of claim 1, further comprising suggesting to the user an increase or decrease of a specific physical activity to implement the remedial action.

7. The method of claim 1, wherein the remedial action is a push notification integrated in an operating software application.

8. A method for improving sleeping habits of a user, the method comprising:

collecting activity data detected via (a) a plurality of smart home devices, (b) a plurality of mobile devices, or (c) both, the activity data being indicative of various physical activities of the user, at least some of the plurality of smart home devices and the plurality of mobile devices being communicatively coupled for sharing the activity data;

correlating the activity data to sleep quality that is specific to the user, the sleep quality including physical aches caused by sleeping posture;

determining, based on the correlating, a sleep effect on the sleep quality of the user;

generating, based on the sleep effect, a sleep-quality indicator;

in response to changes in the activity data, adjusting in real-time the sleep-quality indicator;

causing the sleep-quality indicator to be communicated to the user in real-time during the physical activity, wherein the sleep quality indicator is communicated to the user at least in part in the form of a sleep-health meter generated in the form of a meter image that is displayed on a screen of a mobile device of the user, the meter image being automatically adjusted in real-time to provide a live prescription for better sleep in response to changes in the activity data;

after the user has slept, receiving sleep-quality data for at least one sleep session of the user, the sleep-quality data including at least one of sleep stages, sleep duration, awake hours, and asleep hours;

correlating the sleep-quality data with the activity data to determine a further sleep effect on the sleep quality of the user attributable to one or more of the adjustments of the sleep-quality indicator;

adjusting, based on the further sleep effect, at least one subsequent sleep-quality indicator and subsequent meter image so that later-generated sleep-quality indicators and meter images are personalized to the user's sleep patterns and lifestyle; and increasing at least one of a deep-sleep state and sleep duration based on the adjusting of the sleep-quality indicator.

9. A system comprising:

an electronic interface configured to receive data associated with a physical activity of a user;

a memory storing machine-readable instructions; and a control system including one or more processors configured to execute the machine-readable instructions to:

receive electronically data associated with physical or psychological factors of the user, the data being collected from (a) a plurality of smart home devices, (b) a plurality of mobile devices, or (c) both, the physical or psychological factors being based on at least one physical activity of the user;

identify, based on the data, an effect on sleep quality of the user;

determine, based on the effect, a remedial action for improving sleep quality of the user;

cause the remedial action to be communicated in electronic form to the user in real-time during the physical activity, wherein the remedial action is communicated to the user at least in part in the form of a visual remedial indicator generated in the form of a meter image that is displayed on a screen of a mobile device of the user, the meter image being automatically adjusted in real-time to provide a live prescription for better sleep in response to changes in the data associated with the physical or psychological factors of the user;

automatically implement, without input from the user, at least a part of the remedial action via one or more of the plurality of smart home devices and the plurality of mobile devices;

after the user has slept, receive sleep-quality data for at least one sleep session of the user, the sleep-quality data including at least one of sleep stages, sleep duration, awake hours, and asleep hours;

correlate the sleep-quality data with the data associated with the physical or psychological factors of the user to determine a sleep effect on the sleep quality of the user attributable to one or more of the remedial actions;

adjust, based on the sleep effect, at least one subsequent remedial action and subsequent automatic implementation so that later-computed remedial actions and meter images are personalized to the user's sleep patterns and lifestyle; and increase at least one of a deep-sleep state and sleep duration based on the remedial action.

10. The method of claim 1, wherein the meter image fills up or depletes based on the data.

11. A method comprising:

receiving electronically data associated with physical or psychological factors of the user, the data being collected from (a) a plurality of smart home devices, (b) a plurality of mobile devices, or (c) both, the physical or psychological factors being based on at least one physical activity of the user;

identifying, based on the data, an effect on sleep quality of the user;

determining, based on the effect, a remedial action for improving sleep quality of the user;

causing the remedial action to be communicated in electronic form to the user in real-time during the physical activity, wherein the remedial action is communicated to the user at least in part in the form of a visual remedial indicator generated in the form of a meter image that is displayed on a screen of a mobile device of the user, the meter image comprising (i) a sleep-health meter that represents an overall sleep-quality condition of the user and (ii) a plurality of data health-meters respectively indicative of different sleep-quality contributors, the sleep-quality contributors including at least one user-behavior contributor and at least one environmental contributor, each data health-meter being automatically adjusted in real-time based on the data and contributing to adjustment of the sleep-health meter;

automatically implementing, without input from the user, at least a part of the remedial action via one or more of the plurality of smart home devices or the plurality of mobile devices, wherein the remedial action is selected based on at least one of the data health-meters;

prompting the user, during the day, with live updates derived from the data health-meters to change at least one behavior associated with one of the sleep-quality contributors; and increasing at least one of a deep-sleep state and sleep duration based on the remedial action.

12. The method of claim 11, wherein the at least one user-behavior contributor includes one or more of sleep routine, screen time, physical exercise, diet, wellness, outdoor time, and stress.

13. The method of claim 11, wherein the at least one environmental contributor includes one or more of ambient temperature, ambient light, ambient humidity, and noise level.

14. The method of claim 11, wherein the sleep-health meter ranges from a minimum sleep-health representative of the user being awake all night to a maximum sleep-health representative of the user having the highest chance of a best sleep.

15. The method of claim 11, wherein each of the plurality of data health-meters is presented as a horizontal bar on the screen of the mobile device of the user.

16. The method of claim 11, wherein the remedial action that is automatically implemented comprises at least one of adjusting a bedroom temperature via a smart thermostat, adjusting ambient lighting via smart lights, or adjusting noise levels via a smart virtual home assistant.

17. The method of claim 11, wherein prompting the user during the day comprises providing a reminder to the user to change at least one of outdoor time, physical exercise, screen time, or diet based on a corresponding data health-meter indicating a less than ideal condition.

18. The method of claim 11, further comprising, after the user has slept, receiving sleep-quality data for at least one sleep session of the user and correlating the sleep-quality data with the data associated with the physical or psychological factors to personalize at least one subsequent remedial action to the user's sleep patterns and lifestyle.

* * * * *